United States Patent [19]

McCormick

[11] Patent Number: 5,156,019
[45] Date of Patent: Oct. 20, 1992

[54] FROZEN TISSUE SECTIONING APPARATUS AND METHOD

[76] Inventor: James B. McCormick, 6755 Longmeadow Dr., Lincolnwood, Ill. 60646

[21] Appl. No.: 615,493

[22] Filed: Nov. 19, 1990

[51] Int. Cl.$^5$ .............................................. F25C 5/02
[52] U.S. Cl. ...................................... 62/320; 83/915.5
[58] Field of Search ........................ 62/320; 83/915.5

[56] References Cited

U.S. PATENT DOCUMENTS

| | | | |
|---|---|---|---|
| 3,204,424 | 9/1965 | McCormick | 62/320 |
| 3,233,965 | 2/1966 | McCormick | 83/915.5 X |
| 3,272,348 | 9/1966 | Metz | 83/915.5 X |
| 3,462,969 | 8/1969 | Grasenick et al. | 62/320 X |
| 3,491,638 | 1/1970 | Idlis | 83/915.5 X |
| 3,664,412 | 5/1972 | Zerkle | 62/320 X |
| 4,548,051 | 10/1985 | Moessner | 62/320 |
| 4,979,376 | 12/1990 | Biehl et al. | 83/915.5 X |

FOREIGN PATENT DOCUMENTS

| | | | |
|---|---|---|---|
| 2141129 | 3/1973 | Fed. Rep. of Germany | 83/915.5 |
| 426164 | 10/1974 | U.S.S.R. | 83/915.5 |

*Primary Examiner*—Henry A. Bennet
*Assistant Examiner*—Christopher B. Kilner
*Attorney, Agent, or Firm*—Fitch, Even, Tabin & Flannery

[57] ABSTRACT

Disclosed is an apparatus for slicing tissue sections from a frozen specimen for microscopic analysis or the like without allowing tissue debris or dust to become airborne and thereby transport bacteria or viruses from one specimen to other specimens or to an operator. This is achieved by slicing the specimen while submersed in a subzero dielectric liquid and passing a conveyor, such as a statically charged web or film, adjacent the point of sectioning so that the tissue sections and associated tissue debris generated therewith are attracted to the web and adhere thereto. The conveyor transports the tissue sections, and associated debris adhering thereto, through a sterilizer and staining tanks whereafter the tissue is transferred to a slide for microscopic examination.

25 Claims, 2 Drawing Sheets

FROZEN TISSUE SECTIONING APPARATUS AND METHOD

BACKGROUND OF THE INVENTION

1. Field of the Invention

This invention relates to an apparatus and method for sectioning frozen organic tissue samples under cryogenic conditions.

2. Description of Related Art

It is known in the prior art to freeze tissue samples prior to sectioning in order to allow for greater precision in tissue sectioning. For instance, the tissue sample can be frozen to a particular shape prior to sectioning in order to produce tissue sections of a uniform, desired cross-section. Various apparatus, such as that disclosed in U.S. Pat. Nos. 3,204,424 and 3,213,379, have been developed for freezing tissue specimens in preparation for sectioning in a microtome. It is necessary, therefore, to employ a cryostat microtome which maintains the tissue specimen in a frozen state during sectioning. Current cryostat microtomes, such as that disclosed in U.S. Pat. No. 4,548,051, operate in a cold air environment wherein an enclosure maintains a refrigerated cold air environment within which the microtome is housed. Such cold air microtomes suffer from several shortcomings, as explained below.

A microtome is a piece of precision equipment for making very thin sections (1 to 15 $\mu$m) from tissue. A microtome may have to section large numbers of tissue samples daily. These tissue samples may contain countless viruses and bacteria. Due to the fact that slicing organic tissue thinly necessarily results in the simultaneous generation of some amount of tissue debris or "dust," slicing of large numbers of tissue samples necessarily results in generation of large amounts of tissue debris. Accordingly, conventional cold-air cryostat microtome arrangements have been found to result in large amounts of tissue debris becoming airborne. This tissue debris contains whatever viruses and bacteria that were present in the original tissue specimen. Thus, one problem associated with prior cryostat microtomes is that some originally pure tissue specimens are contaminated by airborne tissue particles of other specimens, thereby greatly reducing the accuracy of analyses and/or examinations of such tissue sections.

Also, due to the precision required in producing such thinly sliced tissue sections, close operator supervision is necessary. Thus, in using conventional cryostat microtomes, operators are required to be exposed to the airborne tissue particles generated upon tissue sectioning. There is, accordingly, a great fear of operator contamination from the viruses and bacteria present in these airborne particles. This fear has been particularly accentuated in recent years by increased cases of hepatitis and AIDS. Thus, operators are currently reluctant to operate conventional microtomes or work near them.

Current microtomes generate significant amounts of tissue debris during sectioning. Thus, there is a need for the ability, in such microtomes, to be able to section large quantities of tissue without allowing the tissue debris generated therewith to become airborne.

SUMMARY OF THE INVENTION

In accordance with the present invention, tissue sections are sliced from a specimen without tissue dust, debris, or other tissue particles, collectively referred to herein as debris, becoming airborne and thereby transporting bacteria such as tuberculosis and fungi, or viruses such as AIDS or hepatitis. Preferably, this is achieved by providing a vessel or other suitable container which is filled with a dielectric fluid maintained at a subzero temperature. A microtome or other suitable sectioning device is submersed in the dielectric fluid, slicing the specimen being sectioned while submersed in a dielectric liquid and a tissue conveyor, generally in the form of a web or film, is passed closely adjacent to the microtome and an attractive charge is created between the specimen and the conveyor that causes the removed tissue section and any tissue debris generated to be attracted to and adhered to the conveyor. The conveyor, with the tissue section and associated debris adhered thereto, is transported through a sterilizer where the tissue section and debris are sterilized, preferably either by means of radiation or by means of a strong oxidizing lamp generating ozone, while keeping the chemistry and antigenicity of the tissue section intact. The sterilized tissue section and tissue particles are subsequently transported through staining tanks whereat routine or special stains are applied, and finally to a mounting station at which the sections are removed from the conveyor and are mounted for later analysis, usually by potting the sample in a methacrylate or other suitable monomer that is polymerized by exposure to ultraviolet light. Conventional microscopic examination on a glass slide may then be made.

BRIEF DESCRIPTION OF THE DRAWINGS

This invention will be more fully understood, and further objects and advantages thereof will become apparent in the following detailed description of preferred embodiments of the invention illustrated in the accompanying drawings, wherein like elements are referenced alike.

DETAILED DESCRIPTION OF THE PREFERRED EMBODIMENTS

Figure 1:
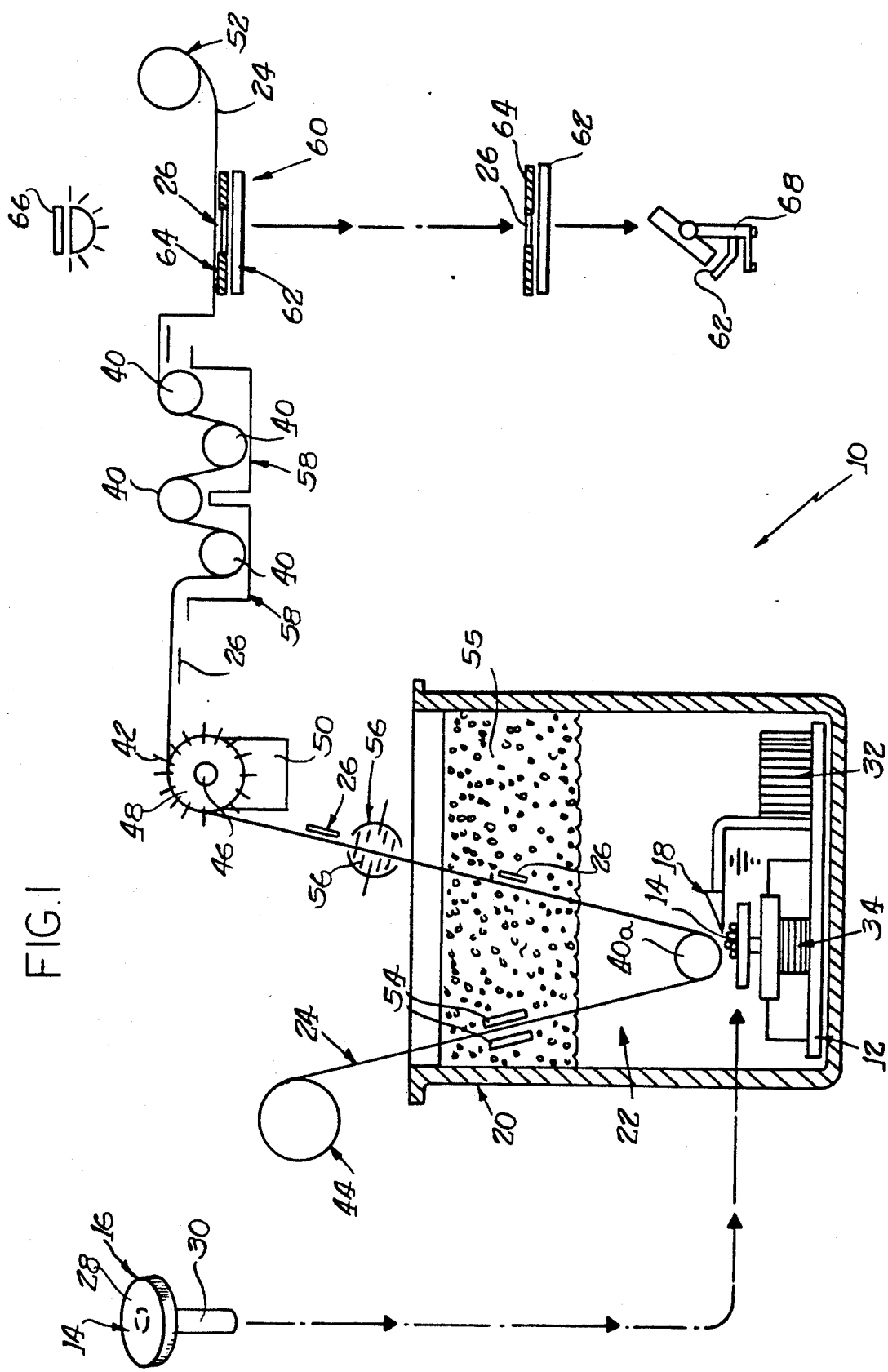
FIG. 1 is an illustration of an embodiment of a cyrostat microtome apparatus constructed in accordance with the present invention.

FIG. 1 shows a preferred embodiment of a cryostat microtome apparatus constructed according to the principles of the present invention. The overall apparatus is generally designated at 10, while the microtome itself, which performs the tissue sectioning, is generally designated at 12.

The microtome 12 is preferably of the kind already known in the art, wherein a tissue specimen 14 is mounted to a tissue block 16 which oscillates beneath a stationary blade 18 to section the tissue specimen 14 thereon. As shown in FIG. 1, in accordance with the present invention, the microtome 12 is housed within an insulated tank 20 and submersed in a dielectric oil 22. Preferably, the dielectric oil 22 is at a subzero temperature so that a frozen tissue specimen remains frozen during sectioning.

A conveyor 24 is mounted for passage immediately adjacent to the stationary blade 18, and an attractive charge is established between the specimen and the conveyor 24 so that tissue section 26, and the tissue debris generated therewith when severed from the specimen, will be attracted to and adhered to the conveyor 24, generally by electrostatic attraction. The advancement of the conveyor 24 is synchronized with the rate of tissue section generation so that each tissue section 26, with its associated tissue debris, occupies a separate space on the conveyor 24 separated from other tissue sections and their associated debris.

The tissue sections 26, electrostatically adhering to the conveyor 24, are transported out of the subzero environment of the insulated tank 20 upon advancement of the conveyor 24, and are immediately sterilized in a suitable sterilizer 56 to sterilize any bacteria or viruses present. The sterilized tissue sections 26 may subsequently pass through additional processing sections, as is conventional in the art, whereafter they are finally transported to a mounting station 60 whereat sections are mounted for ultraviolet or microscopic examination.

This arrangement allows large quantities of tissue to be rapidly sectioned without allowing the tissue debris generated therewith to become airborne and preventing the debris from one section to come into contact with, and thereby contaminating, another tissue section. The present invention is particularly well-suited for making series sections, which are a series of sections taken from the specimen in question, without gaps or intervals between the sections produced.

With reference to FIG. 1, a conventional microtome 12 is employed to section a frozen tissue specimen 14. The microtome 12 is mounted to the bottom of an insulated tank 20, which tank contains dielectric oil 22 at a level sufficient to completely submerse the microtome 12 therein. The oil 22 is maintained generally between $-10°$ C. and $-40°$ C., and preferably at approximately $-20°$ C., by a suitable refrigeration unit, not shown, so that the tissue specimen 14 and tissue sections 26 remain frozen while within the insulated tank. Any dielectric oil that is sufficiently fluid at these temperatures, may be employed. The insulation in the tank 20 is provided to assist in maintaining the subzero temperature therein.

As stated above, the microtome 12 includes a tissue block 16 upon which a tissue specimen 14 is mounted, and which oscillates beneath a stationary blade 18. The tissue block 16 is preferably comprised of a stainless steel disc 28 upon which the specimen is mounted and a depending mandrel 30 which supports the disk. The tissue block 16 component of the microtome is removably attached to the microtome 12 by insertion of the mandrel 30 therein. A standard tool changer can be employed to insert successive tissue blocks 16 with specimens 14 mounted thereon in the microtome for sectioning, and to remove the tissue blocks 16 from the microtome 12 upon completion of the sectioning.

With the tissue block 16 inserted in the microtome 12, sectioning is accomplished by employing a linear step motor 32 to oscillate the tissue block 16 laterally beneath the stationary blade 18 slicing the tissue specimen 14 with each lateral oscillation. Also, a micrometer feed step motor 34 is employed to adjust the transverse position of the tissue block 16 relative to stationary blade 18 between successive lateral oscillations. That is, the thickness of the generated tissue sections 26 can be varied, as desired, by adjusting the micrometer feed step motor 34 to move the tissue block 16 transversely either a large or small amount between successive slicings. Accordingly, tissue specimens 14 are sectioned in a rapid, automated process while retained in a frozen state during sectioning.

With each such tissue sectioning, there is usually generated a corresponding quantity of tissue debris. To prevent such tissue debris from becoming airborne or contaminating other tissue sections, a conveyor 24, having a surface charge thereon, is passed in close proximity to the microtome 12 to cause the tissue sections 26, and associated tissue debris generated therewith, to electrostatically adhere to the conveyor 24.

Figure 2:
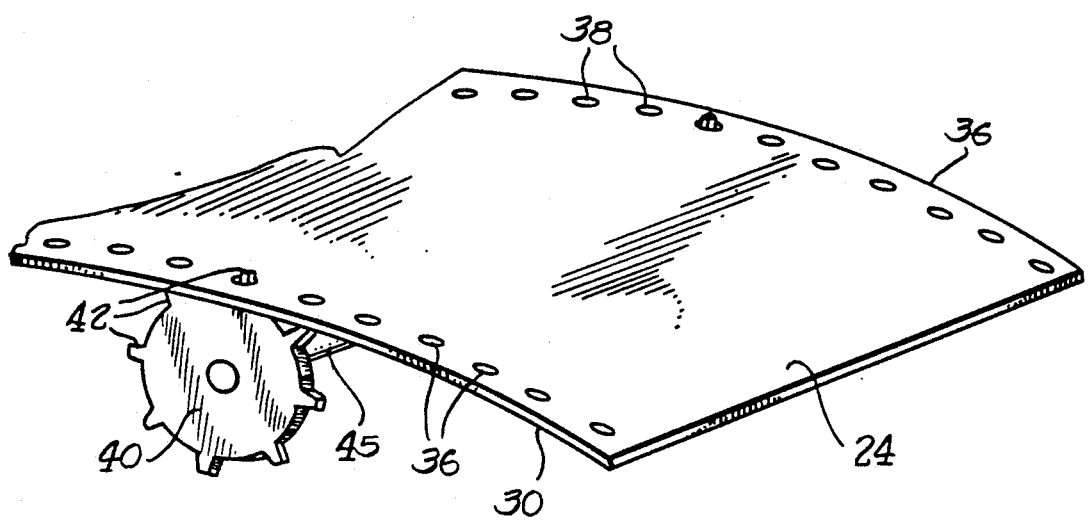
FIG. 2 is an enlarged perspective view of the sprocketed wheels employed in accordance with the embodiment of FIG. 1.

The conveyor 24 can be advanced by any suitable means. In one embodiment, as seen in FIG. 2, to provide for advancement of the conveyor which is in the form of a flexible web, the conveyor 24 is fenestrated adjacent both its lateral sides 36. That is, sprocket holes 38 are provided along the length of the lateral sides 36 of the conveyor 24, which are evenly spaced from one another and which receive sprockets 42 therein. As seen in FIG. 1, the conveyor 24 is preferably passed around several sprocketed wheels 40. The registration of the sprockets 42 and the sprocket holes 38 maintains accurate alignment of the conveyor 24. These sprocketed wheels 40 are located at opposing ends of axles 45. As shown in FIG. 2, this sprocket arrangement allows sufficient clearance between the conveyor 24 and axles 45 so that the tissue sections 26, adhering to the underside of the conveyor 24, do not come in contact with the axles 45 when passing thereover.

In the embodiment of FIG. 1, the conveyor 24 is driven by a drive roller 46 having sprocketed drive wheels 48 at its opposing ends. The drive roller 46 is, in turn, driven by a linear motor 50 which is provided with logic control operating in conjunction with feedback from the micrometer to advance the conveyor 24 at the rate of tissue section generation. Thus, as seen in FIG. 1, the conveyor 24 is initially wound about a supply reel 44, and is ultimately received upon a take-up reel 52, after passing around several sprocketed wheels 40 under the action of the drive roller 46. That is, the conveyor 24 makes a single pass from the supply reel 44 to the take-up reel 52. In the embodiment described herein, the conveyor is plastic, but other materials may be employed as well.

It is to be understood that other forms of drive mechanisms, such as a driven take-up reel, might be employed. It is also contemplated that the conveyor could be an endless belt.

To induce the electrical surface charge on the conveyor 24, which causes the tissue sections to adhere thereto, the conveyor 24 is passed between two positively charged grids 54. The positively charged grids 54 are positioned on opposing sides of the conveyor 24, and have a positive charge maintained on their surface. Thus, as the conveyor 24 passes between the positively charged surfaces, a positive electrostatic charge is induced on the surface of the conveyor 24. After the conveyor 24 has a positive electrostatic charge imposed thereon, it passes into the dielectric oil 22. Since the oil 22 is a dielectric, the static charge does not dissipate significantly therein, and, thus, a positive surface charge is maintained on the surface of the conveyor 24.

While the embodiment of FIG. 1 depicts a positive surface charge imposed on the surface of the conveyor 24, other methods of electrostatic adhesion are equally well suited for such apparatus. For instance, a negative surface charge can be imposed on the conveyor 24, or either negative or positive surface charges can be imposed on the specimen 14 instead, or opposite surface charges can be imposed on the conveyor 24 and specimen 14. Each of these provide the requisite electrostatic adhesion between the tissue sections 26 and conveyor 24. Also, while charged grids are depicted in the preferred embodiment, several alternate means for inducing electrostatic charges on materials are equally well suited for carrying out the present invention.

With continued reference to FIG. 1, the conveyor 24, having a surface charge now imposed thereon, subsequently passes around a sprocketed wheel 40a which brings the conveyor 24 in close proximity with the stationary blade 18 of the microtome 12. The influence of the surface charge imposed on the surface of the conveyor 24 causes the tissue sections 26, and associated tissue debris generated therewith, to migrate toward the conveyor 24 and electrostatically adhere thereto. The tissue sectioning and the initial electrostatic adhesion of the tissue sections 26 to the conveyor 24 occur within the subzero dielectric oil 22, so that the tissue sections 26 remain frozen, and, therefore, noninfectious.

Since the conveyor 24 is advanced in relation to the rate of tissue section generation, as discussed above, each tissue section 26, and the tissue debris generated with that particular section, occupies a separate space along the length of the conveyor 24 separated from the other tissue sections and their debris. Also, the electrostatic adhesion between the tissue section 26 and the conveyor 24 prevents tissue and tissue debris from becoming airborne after exiting the insulated tank 20.

As the conveyor 24 advances, the tissue sections 26 continue to adhere and are advanced therewith. As shown in FIG. 1, the apparatus preferably includes a headspace 55 in insulated tank 20 which may be filled with a suitable gas, which may be a treatment gas, e.g., chlorine for sterilizing, ozone for oxidizing or the like, or an inert gas such as nitrogen. Preferably, the gas is maintained at a subzero temperature to maintain the specimen and debris in a frozen state. It is appreciated that several additional sprocketed wheels 40 may be employed to loop the conveyor 24 one or more times within the headspace 55 so as to provide additional reaction time therein.

Upon exiting the insulated tank 20, the tissue sections 26 are exposed to radiation to sterilize any bacteria or viruses that may be present. As shown in FIG. 1, the tissue sections 26 are passed between radiation emitters 56. The radiation emitters 56 may be of any type well-known in the art that is capable of providing the requisite radiation necessary to sterilize the tissue sections 26. Alternatively, oxidizing lamps could be employed in place of the radiation emitters 56 wherein the oxidizing lamps generate ozone which sterilizes the tissue sections 26 while keeping the chemistry and antigenicity of the tissue sections 26 intact. To assure that the complete tissue section 26 is exposed to sufficient sterilization, it is desirable to provide the radiation emitters 56 or oxidizing lamps on either side of the conveyor 24 so that both sides of the tissue section 26 are radiated directly. Any other suitable sterilizing means may be employed as well.

After sterilization, the tissue sections are next prepared for viewing. With reference to FIG. 1, it is seen that, upon exiting the radiation emitters 56, the tissue specimens pass around the drive wheel 48 (discussed earlier) and then are passed into and out of staining and fixing tanks 58. In practice, it is common for the tissue section to be passed through a first staining tank 58 which contains a stabilizer to inhibit cell decay, with the tissue sections 26 subsequently passed through a plurality of additional staining tanks 58 depending upon the tissue being examined. Whereas the illustrative embodiment of FIG. 1 depicts two staining tanks 58, as is well known in the art, any number of staining tanks may be employed depending upon the analysis to be performed.

Sprocketed wheels 40 are employed to move the conveyor 24, with the tissue specimens 26 adhering thereto, into and out of the staining tanks 58, as shown in FIG. 1. The number of sprocketed wheels 40 employed will vary depending upon the number of staining tanks 58 employed.

After undergoing staining, the tissue sections 26 are transported to a mounting station 60 at which the now sterilized and stained tissue sections are transferred from the conveyor 24 to a glass slide 62. To assure adhesion of the tissue sections 26 to the glass slide 62, a methacrylate monomer 64 covers the surface of the glass slide 62. The tissue section 26 is potted in the methacrylate monomer 64 which is then polymerized by exposure to ultraviolet light emitted from an ultraviolet light source 66. This solidifies the methacrylate monomer 64 with the tissue section 26 therein such that the tissue section 26 is affixed to the glass slide 62 for conventional viewing under a microscope 68.

Accordingly, tissue sections 26 can be taken from a tissue specimen 14 and analyzed under a microscope 68 without an operator being exposed to bacteria or viruses, and without tissue debris from one section contaminating another section.

While the invention has been described with reference to a preferred embodiment, it will be understood to those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A cryogenic microtome apparatus for sectioning frozen tissue specimens, comprising:
    container means adapted to contain a dielectric fluid;
    microtome means submersed in the dielectric fluid for sectioning a tissue section from a frozen tissue specimen;
    a conveyor means for conveying the tissue section from said container means;
    means for mounting said conveyor means immediately adjacent said microtome means; and
    means for causing adhesion between a tissue section and associated debris and said conveyor means.

2. A microtome apparatus in accordance with claim 1 wherein said apparatus includes means for sterilizing the tissue section and associated debris upon transportation from the dielectric fluid while maintaining their chemistry and antigenicity.

3. A microtome apparatus in accordance with claim 2 wherein, after undergoing sterilization, tissue sections and their associated tissue particles are transported to a mounting station for analysis.

4. A microtome apparatus in accordance with claim 1 wherein the apparatus includes means for synchronizing the movement of said conveyor with the rate of tissue section generation.

5. A microtome apparatus in accordance with claim 4 wherein said means for synchronizing the movement of said conveyor with the rate of tissue section generation includes a logic-controlled stepping motor which advances said film a given distance for each tissue section generated.

6. A microtome apparatus in accordance with claim 1 wherein said means for sectioning organic tissue includes a stationary tissue slicing means and further includes a moving tissue block adjacent each other, said organic tissue being mounted on said block.

7. A microtome apparatus in accordance with claim 6 wherein an oscillating drive means oscillates the tissue block linearly with respect to said tissue slicing means.

8. A microtome apparatus in accordance with claim 1 wherein said conveyor means includes a dielectric film.

9. A microtome apparatus in accordance with claim 8 wherein said dielectric film includes an elongated film web of plastic.

10. A microtome apparatus in accordance with claim 9 wherein said film and section have opposite electrical surface charges imposed thereon.

11. A microtome apparatus in accordance with claim 1 wherein said conveyor means includes a continuous, traveling web of dielectric solid passing adjacent said microtome means at a point on its path of travel.

12. A microtome apparatus in accordance with claim 2 wherein the apparatus includes a series of tanks for receiving staining and fixing agent and means for passing said conveyor therethrough.

13. A microtome apparatus in accordance with claim 2 wherein said means for sterilizing said tissue sections adhering to the dielectric solid includes an oxidizing lamp for oxidizing tissue passing in close proximity to the oxidizing lamp.

14. A microtome apparatus in accordance with claim 1 including a means for transfer attaching the tissue section from the plastic web to a glass slide with a U.V. polymerized resin mounting material.

15. A microtome apparatus in accordance with claim 3 including gas- and liquid-phase processing means for processing said tissue prior to said transportation thereof to a mounting station for analysis.

16. A microtome apparatus in accordance with claim 1 wherein said dielectric fluid is maintained between approximately −40° C. and 0° C., preferably at −20° C.

17. A method for the preparation of tissue sections comprising:
    sectioning a tissue specimen at a sectioning station to provide a tissue section and associated debris;
    adhering said section and debris to the surface of a conveyor;
    conveying said section and associated debris to a mounting station remote from said sectioning station;
    removing said tissue section from said conveyor at said mounting station; and
    mounting said tissue to provide a microscopic slide.

18. A method in accordance with claim 17 wherein the sectioning station is immersed in a dielectric fluid.

19. A method in accordance with claim 17 wherein the tissue specimen is frozen.

20. A method in accordance with claim 18 wherein the dielectric fluid is at a temperature of between about −10° C. and about −40° C.

21. A method for sectioning organic tissue under cryogenic conditions, comprising:
    submersing a frozen tissue specimen to be sectioned in a subzero dielectric liquid means;
    passing a dielectric film in proximity with said frozen tissue specimen;
    imposing an electrical surface charge to one of said dielectric film and said organic tissue such that as tissue is sectioned, the tissue section and its associated tissue particles electrostatically adhere to the dielectric film passing in proximity with the tissue;
    sectioning said tissue by sectioning means while the tissue is submersed in said dielectric liquid; and
    transporting the sectioned tissue and tissue particles from the dielectric liquid.

22. A method in accordance with claim 21 including the step of sterilizing the tissue sections while they are electrostatically adhered to the film.

23. A method in accordance with claim 22 including the step of transporting the sterilized tissue sections to a mounting station for viewing.

24. A method in accordance with claim 21 including the step of passing tissue sections through gas- and liquid-phase processing means.

25. A method in accordance with claim 21 including the step of synchronizing the movement of said dielectric solid with the rate of tissue section generation.

* * * * *